(12) United States Patent
Gurley et al.

(10) Patent No.: US 6,277,870 B1
(45) Date of Patent: Aug. 21, 2001

(54) USE

(75) Inventors: David Gurley, Lima; Thomas Lanthorn, Pittsford, both of NY (US)

(73) Assignee: Astra AB (SE)

( * ) Notice: Subject to any disclaimer, the term of this patent is extended or adjusted under 35 U.S.C. 154(b) by 0 days.

(21) Appl. No.: 09/071,826

(22) Filed: May 4, 1998

(51) Int. Cl.[7] ............ A61K 31/44; A61K 31/405; C07D 211/68; C07D 213/02; C07D 401/00

(52) U.S. Cl. ............ 514/343; 514/415; 546/193; 546/194; 546/257; 546/279.4

(58) Field of Search .................. 546/193, 194, 546/257, 279.4; 514/343, 415

(56) References Cited

FOREIGN PATENT DOCUMENTS

| PCT/SE99/ | | |
|---|---|---|
| 00700 | 4/1989 | (WO) . |
| 96/06098 * | 2/1996 | (WO) . |
| 97/30998 * | 8/1997 | (WO) . |
| 99/03859 * | 1/1999 | (WO) . |

OTHER PUBLICATIONS

Kooyman et al, "5–Hydroxyindole slows desensitization of the $5-HT_3$ receptor. . ." Br. J. Pharmacol. vol. 108, pp. 287–289 (1993).

Schrattenholz et al, "Agonist Responses of Neuronal Nicotinic Acetylcholine. . ." Molecular Pharmacology, vol. 49, pp. 1–6 (1996).

Kuntzweiler et al, rapid Assessment of Ligand Actions with Nicotinic AcetyLcholine Receptors Using Calcium Dynamics and FLIPR, Drug Development Research, Issued May 1, 1998, vol. 44, pp. 14–20, May.*

Ospina et al, Calcium Regulation of Agonist Binding to alpha 7–Type Nicotinic Acetylcholine Receptors in Adult and Fetal Rat Hippocampus, Journal of Neurochemistry, vol. 70, No. 3, Issued Mar. 1998.*

* cited by examiner

Primary Examiner—Howard C. Lee
Assistant Examiner—Everett White
(74) Attorney, Agent, or Firm—Richard V Person

(57) ABSTRACT

The present invention relates to pharmaceutical compositions comprising a positive modulator of a nicotinic receptor agonist, said positive modulator having the capability to increase the efficacy of the said nicotinic receptor agonist.

2 Claims, 4 Drawing Sheets

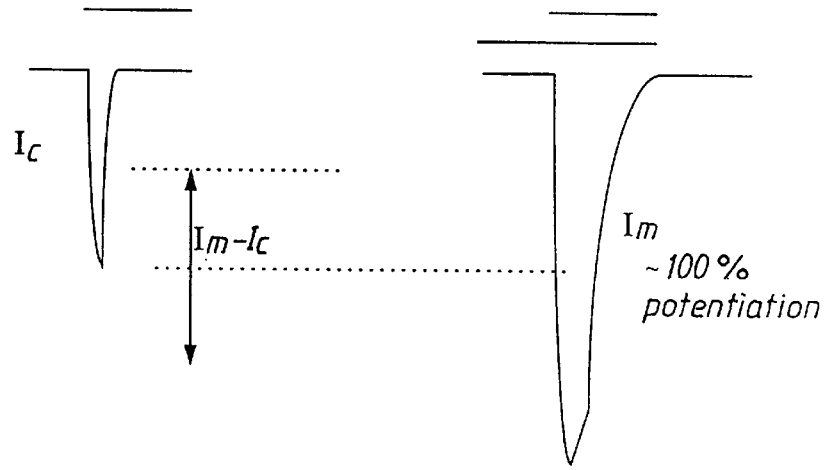
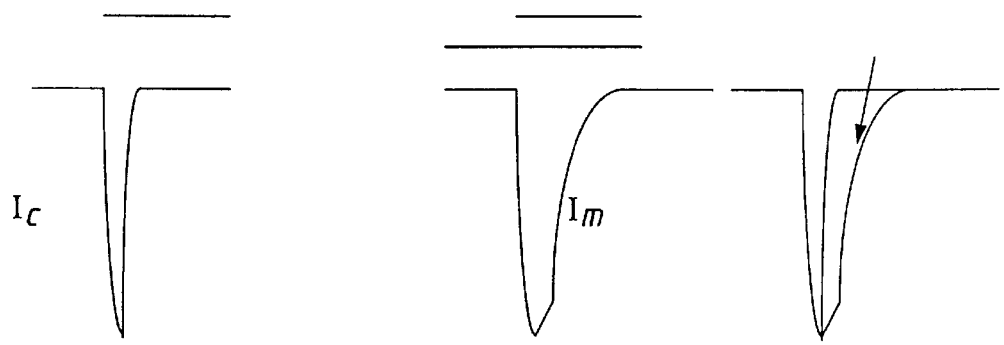

Fig. 3
Agonist Dose-Response Curves in the Presence and Absence of 5-OH-indole
Mouse nAChRα7
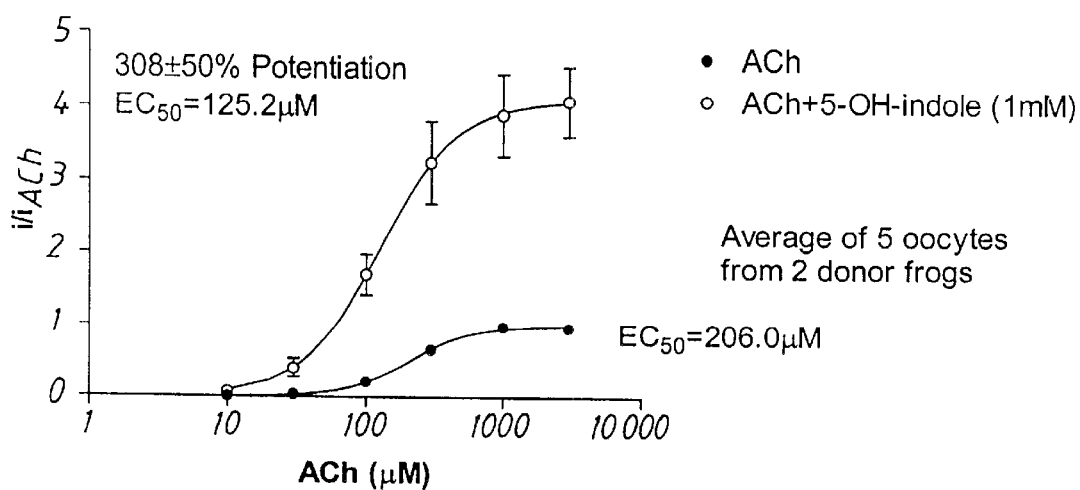
Human nAChRα7
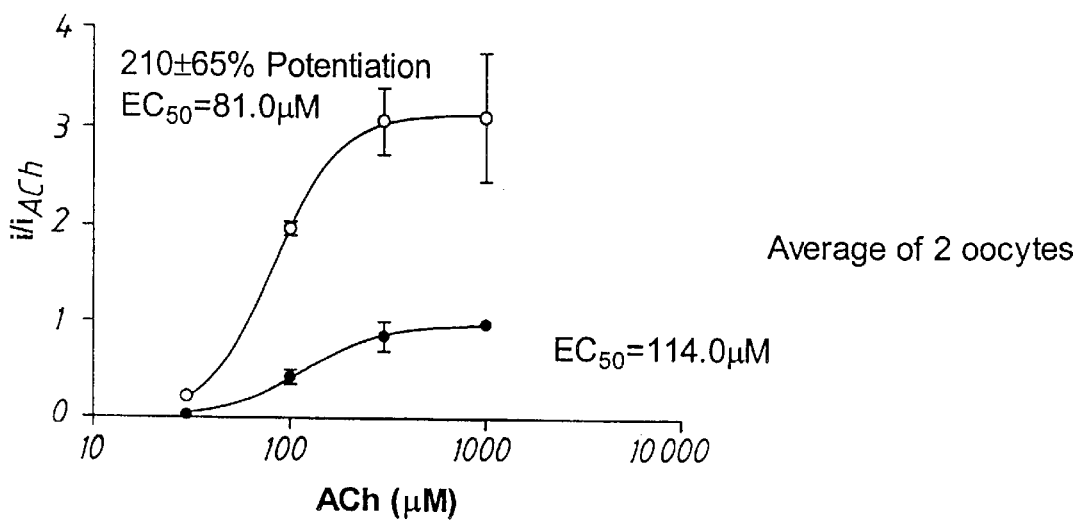
$i_{ACh}$ = extrapolated max of ACh curve

Modulation by 5-OH-indole:
Similar Activity on nAChR α7 from Human, Rat and Chick Expressed in Oocytes
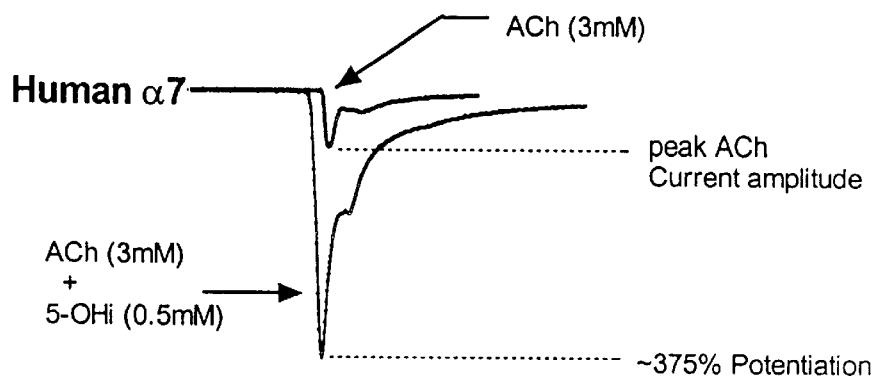
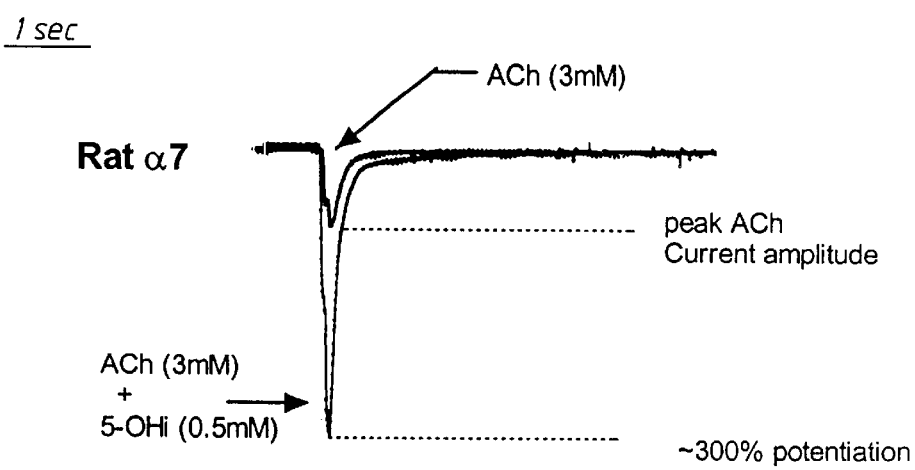
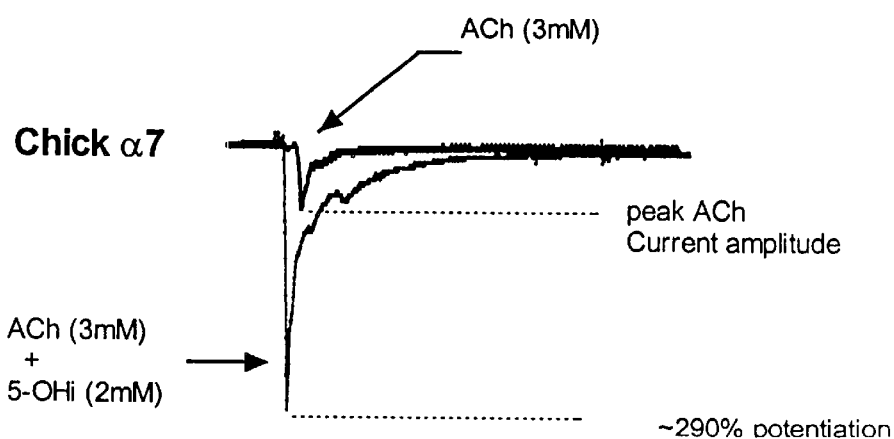

Effect of 5-OH-indole on ACh and AR-R 17779-gated Current
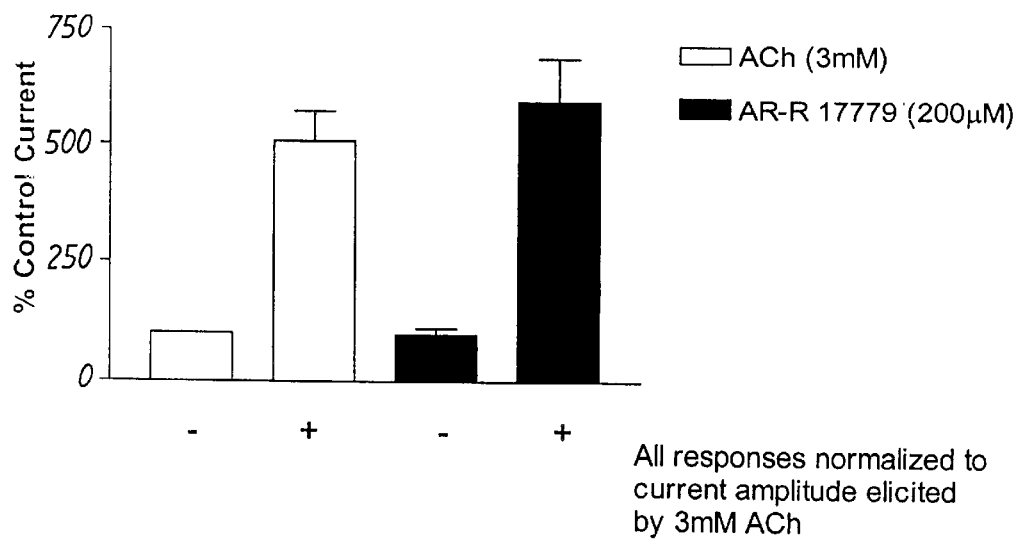
All responses normalized to current amplitude elicited by 3mM ACh
Calcium Influx in α7-HEK293
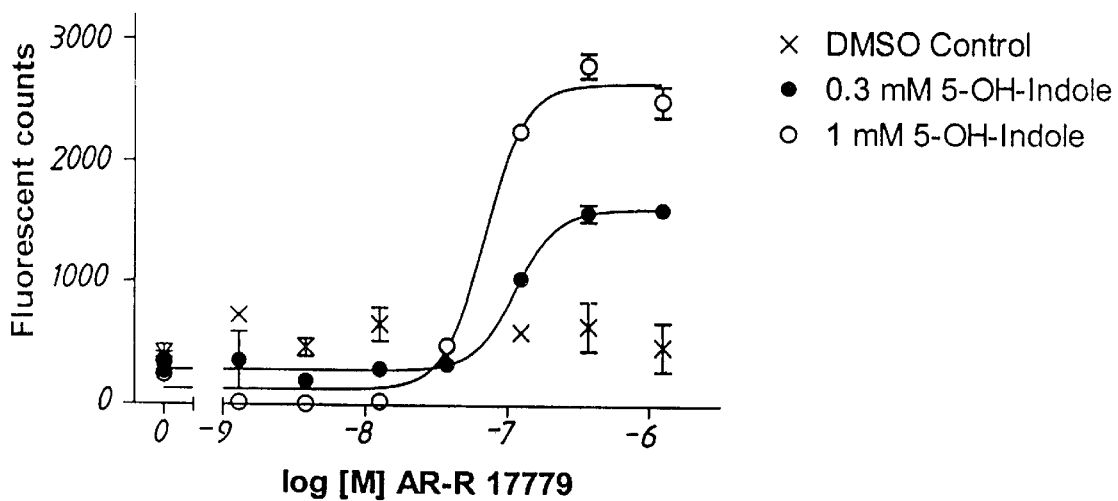

USE

TECHNICAL FIELD

The present invention relates to pharmaceutical compositions comprising a positive modulator of a nicotinic receptor agonist, said positive modulator having the capability to increase the efficacy of the said nicotinic receptor agonist.

BACKGROUND ART

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits (for reviews, see Colquhon et al. (1997) Advances in Pharmacology 39, 191–220; Williams et al. (1994) Drug News & Perspectives 7, 205–223; Doherty et al. (1995) Annual reports in Medicinal Chemistry 30, 41–50). Members of the nAChR gene family have been divided into two groups based on their sequences; members of one group are considered β subunits, while a second group are classified as α subunits (for reviews, see Karlin & Akabas (1995) Neuron 15, 1231–1244; Sargent (1993) Annu. Rev. Neurosci. 16, 403–443). Three of the α subunits, α7, α8 and α9, form functional receptors when expressed alone and thus presumably form homooligomeric receptors.

An allosteric transition state model of the nAChR involves at least a resting state, an activated state and a "desensitized" closed channel state (Williams et al., supra; Karlin & Akabas, supra). Different nAChR ligands can thus differentially stabilize the conformational state to which they preferentially bind. For example, the agonists ACh and (−)-nicotine stabilize the active and desensitized states.

Changes of the activity of nicotinic receptors has been implicated in a number of diseases. Some of these, e.g. myasthenia gravis and ADNFLE (autosomal dominant nocturnal front lobe epilepsy) (Kuryatov et al. (1997) J. Neurosci. 17(23):9035–47), are associated with reductions in the activity of nicotinic transmission either through a decrease in receptor number or increased desensitization, a process by which receptors become insensitive to the agonist. Reductions in nicotinic receptors have also been hypothesized to mediate cognitive deficits seen in diseases such as Alzheimer's disease and schizophrenia (Williams et al., supra). The effects of nicotine from tobacco are also mediated by nicotinic receptors. Increased activity of nicotinic receptors may reduce the desire to smoke.

However, treatment with nicotinic receptor agonists which act at the same site as ACh is problematic because ACh not only activates, but also blocks receptor activity through processes which include desensitization (for a review, see Ochoa et al. (1989) Cellular and Molecular Neurobiology 9, 141–178) and uncompetitive blockade (open-channel block) (Forman & Miller (1988) Biophysical Journal 54(1):149–58). Furthermore, prolonged activation appears to induce a long-lasting inactivation. Therefore agonists of ACh can be expected to reduce activity as well as enhance it. At nicotinic receptors in general, and, of particular note, at the α7-nicotinic receptor, desensitization limits the duration of current during agonist application.

BRIEF DESCRIPTION OF THE DRAWINGS

FIG. 1

Model of current traces elicited by agonist, representing determination of increase in agonist efficacy by determination of current amplitude. Bars denote duration of application of compounds.

FIG. 2

Model of current traces elicited by agonist, representing determination of increase in agonist efficacy by determination of "area under the curve". Arrow indicates overlay of ACh current and ACh+modulator current. Bars denote duration of application of compounds.

FIG. 3

Effect of 5-hydroxyindole on ACh activity on the α7-nicotinic receptor. The current value of 100% is the extrapolated maximum from the ACh curve.
(●) ACh
(○) ACh+0.5 mM 5-hydroxyindole

FIG. 4

Effect of 5-OHi on "area under the curve" for saturating concentration of agonist.

FIG. 5

Effect of 5-hydroxyindole on ACh (open staples) and AR-R-17779 (filled staples) activity on the α7-nicotinic receptor.

FIG. 6

Effect of nAChR α7 modulator on agonist activity as measured by $Ca^{2+}$ flux through nAChR α7 expressed in HEK-293 cells. Filled box is signal obtained in the absence of agonist and the absence of modulator. Filled staples is signal obtained in the presence of agonist alone (no modulator). Open box is signal obtained in the presence of agonist and modulator.

DISCLOSURE OF THE INVENTION

It has surprisingly been found that certain compounds, e.g. 5-hydroxyindole (5-OHi), can enhance the efficacy of agonists at nicotinic receptors. This increase in efficacy can be greater than 2-fold. It is believed that compounds having this type of action (hereinafter referred to as "positive modulators") will be particularly useful for treatment of conditions associated with reductions in nicotinic transmission. In a therapeutic setting such compounds could restore normal interneuronal communication without affecting the temporal profile of activation. In addition, they would not produce long-term inactivation as prolonged application of agonist may.

The presence of this efficacy enhancing activity could not be predicted by the prior art. Albuquerque et al. have reported on another allosteric site on nicotinic receptors, which they call a "noncompetitive agonist" site. Compounds acting at this site are also called "allosterically potentiating ligands" (APL's). Compounds which appear to act at this site include several cholinesterase inhibitors, codeine, and 5-HT. It has been stated that activity via this noncompetitive agonist site "does not affect the level of maximum response to ACh; it shifts the dose-response curve to the left" (Maelicke & Albuquerque (1996) DDT, vol. 1, 53–59). In specific distinction, compounds acting at the discovered site increase the maximum response to ACh (its efficacy).

Another distinction between APL's and the present invention is the effect they have on total current (as measured by area under the curve) in the presence of a saturating concentration of agonist. APL's have little to no effect on area under the curve on nAChR α7 expressed in oocytes; 8–10% increases in area under the curve for a 1 second agonist application have been observed. In contrast, 5-OHi causes a robust increase in area under the curve (~400% increase) under the same conditions (see FIG. 4).

Specificity of the effect within the nicotinic receptor family is yet another distinguishing characteristic between APL's and the invention. APL's exert there positive modulatory effect on all nicotinic receptors tested, including muscle type ($\alpha 1\beta\delta\epsilon$), whereas no positive modulatory effect has been observed with 5-OHi at either of these receptor subtypes.

At some non-nicotinic receptors, compounds have been found which can decrease receptor desensitization. At AMPA-type excitatory amino acid receptors, compounds such as cyclothiazide, some lectins like wheat-germ agglutinin, piracetam-like nootropics, and AMPAkines have been shown to decrease desensitization (Partin et al. (1993) Neuron 11, 1069–1082). Glycine has been reported to reduce desensitization of NMDA-type excitatory amino acid receptors (Mayer et al. (1989) Nature 338, 425–427). However, compounds which decrease desensitization on one receptor group have been found, in general, not to have the same affect on other receptor groups. For instance cyclothiazide has little or no effect on the NMDA and KA subtypes of glutamate receptors (Partin et al. (1993) Neuron 11, 1069–1082); moreover cyclothiazide is found to block 5-$HT_3$ receptors (D. A. Gurley, unpublished results). Glycine has no effect on 5-$HT_3$ receptors (Gurley and Lanthom, (in press) Neurosci. Lett.).

The site was discovered using a compound (5-OHi) which is known to decrease desensitization at the 5-$HT_3$ receptor (Kooyman. A. R. et al. (1993) British Journal of Pharmacology 108, 287–289). However, only one other compound which produces or increases activity at the 5-$HT_3$ receptor, 5-HT itself, has been reported to increase activity at nicotinic receptors (Schrattenholz et al. (1996) Molecular Pharmacology 49, 1–6) although this activity has never been reported in Xenopus oocytes. Most agonists at the 5-$HT_3$ receptor have no activity or are antagonists at nicotinic receptors (unpublished results). In addition, the present inventors have been unable to reproduce the finding that 5-HT increases activity at a nicotinic receptor. Therefore the enhancing effect of 5-OHi at nicotinic receptors could not have been predicted.

Consequently, the present invention provides in a first aspect to a pharmaceutical composition comprising a positive modulator of a nicotinic receptor agonist together with a pharmaceutically acceptable carrier. For the purposes of the present invention, the term "positive modulator" or "positive modulator of a nicotinic receptor agonist" shall be understood as a compound having the capability to increase the maximum efficacy of a nicotinic receptor agonist.

It will be understood that the invention includes compositions comprising either a positive modulator as the only active substance, thus modulating the activity of endogenous nicotinic receptor agonists, or a positive modulator in combination with a nicotinic receptor agonist.

In a preferred form of the invention, the said positive modulator is 5-hydroxyindole.

In another preferred form of the invention, the said nicotinic receptor agonist is an $\alpha 7$-nicotinic receptor agonist. Examples of $\alpha 7$-nicotinic receptor agonists are known in the art, e.g. from WO 96/06098 and WO 97/30998.

In a further aspect, the invention provides a method for the treatment of a condition associated with reduced nicotine transmission, by administering to a patient in need of such treatment, a medically effective amount of a positive modulator of a nicotinic receptor agonist, said positive modulator having the capability to increase the efficacy of the said nicotinic receptor agonist.

It will be understood that the said positive modulator can be administered either with the purpose of acting on endogenous nicotine receptor agonists, or in combination with an exogenous nicotinic receptor agonist.

In a further aspect, the invention provides a method for identifying a positive modulator of a nicotinic receptor agonist. Compounds are considered "positive modulators" if, in the presence of saturating concentrations of the nAChR $\alpha 7$ agonist ACh, current is elicited that exceeds 200% of control current (100% potentiation) when measured baseline to peak (see Experimental Methods). Control current is defined as the current elicited by agonist in the absence of modulator. A saturating concentration of ACh is defined as 10-times the $EC_{50}$ for the specific nAChR $\alpha 7$ type used. $EC_{50}$ is defined as the concentration which elicits a half-maximal response. $EC_{50}$ values for nAChR $\alpha 7$ subtypes typically range between 100–300 $\mu$M (Bertrand et al. (1992) Neuroscience Letters 146, 87–90; Peng et al. (1994) Molecular Pharmacology 45, 546–554). Further, compounds are considered "positive modulators" if, in the presence of saturating concentrations of agonist, total current through the receptor (flux) exceeds 200% of control current. One measure of total current is area under the curve (current trace) during an agonist application.

Consequently, the method according to the invention for identifying a positive modulator of a nicotinic receptor agonist, can comprise the steps (a) expressing a nicotinic receptor on the surface of a cell; (b) contacting the said nicotinic receptor with a compound known to be a nicotinic receptor agonist and a compound to be tested for positive modulating activity; (c) determining whether the compound to be tested exhibits a positive modulation on the effect of the said nicotinic receptor agonist resulting in current amplitude (measured baseline to peak) or total current (measured as area under the curve for the current trace) greater than 200% of control (100% potentiation).

In yet a further aspect, the invention provides a method for identifying a compound which is a nicotinic receptor agonist, said method comprising the steps (a) expressing a nicotinic receptor on the surface of a cell; (b) contacting the said nicotinic receptor with a compound to be tested for nicotinic receptor agonist activity, in the presence of a positive modulator of a nicotinic receptor agonist; and (c) determining whether the compound to be tested exhibits nicotinic receptor agonist activity. It will be understood by the skilled person that "nicotinic receptor agonist activity" can be determined by methods known in the art, such as those methods described in the section "Experimental Methods" below.

Experimental Methods (a) Xenopus Oocyte Current Recording

The Xenopus oocyte has provided a powerful means of assessing the function of proteins thought to be subunits of ligand-gated ion-channels. Injection of RNA transcribed from cDNA clones encoding the appropriate receptor subunits, or injection of cDNA in which the coding sequence is placed downstream of a promoter, results in the appearance of functional ligand-gated ion-channels on the surface of the oocyte (see e.g. Boulter et al. (1987) Proc. Natl. Acad. Sci. U.S.A. 84, 7763–7767).

Consequently, one convenient technique to assess the enhancement of nicotinic efficacy is two-electrode voltage-clamp recording from Xenopus oocytes expressing $\alpha 7$-nicotinic receptors from human cRNA.

Xenopus laevis frogs (Xenopus I, Kalamazoo, Mich.) were anesthetized using 0.15% tricaine. Oocytes were removed to OR2 solution (82 mM NaCl, 2.5 mM KCl, 5 mM HEPES, 1.5 mM $NaH_2PO_4$, 1 mM $MgCl_2$, 0.1 mM EDTA; pH 7.4). The oocytes were defolliculated by incubation in 25 ml OR2 containing 0.2% collagenase 1 A (Sigma) two times for 60 min on a platform vibrating at 1 Hz and stored in Leibovitz's L-15 medium (50 μg/ml gentomycin, 10 Units/ml penicillin, and 10 μg/ml streptomycin). Approximately 50 ng of cRNA was injected in each oocyte the following day. cRNA was synthesised from cDNA using Message Machine (purchased from Abion).

The external recording solution consisted of 90 mM NaCl, 1 mM KCl, 1 mM MgCl$_2$, 1 BaCl$_2$, 5 mM HEPES; pH 7.4. Two-electrode voltage-clamp recording was carried out using an Oocyte Clamp amplifier (OC 725C; Warner Instrument, Hamden, Conn.). Oocytes were impaled with two electrodes of 1–2 MΩ tip resistance when filled with 3M KCl. Recordings were begun when membrane potential became stable at potentials negative to −20 mV (resting membrane potentials are less negative when Ba$^{++}$ replaces Ca$^{++}$ in bathing solutions). Membrane potential was clamped at −80 mV. ACh was purchased from Sigma. Oocytes were continuously perfused (5 ml/min) with recording solution with or without ACh.

Current amplitude was measured from baseline to peak. EC$_{50}$ values, maximal effect, and Hill slopes were estimated by fitting the data to the logistic equation using GraphPad Prism (GraphPad Software, Inc., San Diego, Calif.).

Increases in agonist efficacy elicited by a positive modulator can be calculated in two ways:

(1) As percent potentiation of current amplitude which is defined as $100(I_m-I_c)/I_c$ where $I_m$ is current amplitude in the presence of modulator and $I_c$ is current in the absence of modulator (FIG. 1).

(2) As percent potentiation of "area under curve" of an agonist trace. Area under the curve is a common representation of the total ion flux through the channel (FIG. 2). In the example shown in FIG. 2, although current amplitude is not increased, area under the curve is potentiated roughly 100% over control for the duration of the agonist application (b) Ca$^{2+}$ Flux Imaging Imaging of Ca$^{2+}$ flux through nAChR α7 receptors transiently expressed in a cell line is another means of assaying modulator activity.

Cells expressing α7 receptors are grown to confluence in 96 well plates and loaded with fluo-3, a fluorescent calcium indicator. To screen for α7 modulatory activity, the 96 well plate is placed in a fluorescence imaging plate reader (FLIPR) and test compounds along with an α7 agonist are applied simultaneously to all wells. Receptor activation is measured by calcium influx into cells which is quantified by the increase in fluorescence intensity of each well, recorded simultaneously by the FLIPR. A modulatory effect is determined by the increase in fluorescence over that of agonist alone. Similarly, to test for nAChR α7 agonist activity, test compounds along with an α7 modulator are applied simultaneously to all wells. Receptor activation is measured by calcium influx into cells which is quantified by the increase in fluorescence intensity of each well, recorded simultaneously by the FLIPR. An agonist effect is determined by the increase in fluorescence over that of modulator alone.

EXAMPLE 1

Changes in efficacy of nicotinic agonists was assessed by measuring the combined effects of a nicotinic agonist with test compounds. In general, the protocol consisted of pretreatment with test compound plus coapplication of agonist and test compound. 5-hydroxyindole was tested at 500 μM against a range of concentrations of ACh. ACh was first tested by itself so that an EC$_{50}$ and maximal response could be determined. Then the same concentrations of ACh were applied along with 5-OH-indole. The results (FIG. 3) were that the maximal response to ACh was increased (maximum amplitude increased 2-fold).

The effect of 5-OHi (0.5 mM) on "area under curve" for saturating concentration of agonist (3 mM ACh) was determined. 5-OHi caused a robust increase in area under the curve (~400% increase) (FIG. 4).

Applied by itself, 5-hydroxyindole did not induce current in oocytes injected with cRNA for wild-type α7 nicotinic receptors.

EXAMPLE 2

The effect of 5-hydroxyindole on various nicotinic agonists was tested. The increase in efficacy afforded by 5-hydroxyindole was seen with all nicotinic agonists tested, e.g. AR-R 17779 (FIG. 5). Open boxes current elicited by ACh (3 mM) with (+) and without (−) modulator. Solid boxes current elicited by a nicotinic agonist designated AR-R 17779 (100 μM) with (+) and without (−) modulator. Modulator in this instance was 1 mM 5-OHi.

Compounds tested with similar results include (−)-nicotine and choline (data not shown). Therefore the effect appears to be general for any cholinergic agonist.

EXAMPLE 3

The increase in efficacy afforded by 5-hydroxyindole was not seen on any other nicotinic receptors, e.g. mouse muscle-type nicotinic receptors.

EXAMPLE 4

A series of related compounds were tested for positive modulation on ACh activity. Only a few compounds retained efficacy enhancing activity. In particular, serotonin (5-HT) did not increase efficacy. This preliminary analysis of close analogues indicates a fairly tight structure-activity relationship, suggesting a selective site of action.

EXAMPLE 6

Effect of nAChR α7 modulator on agonist activity was measured by Ca$^{2+}$ flux through nAChR α7 expressed in HEK-293 cells. The nicotinic agonist designated AR-R-17779 was used. The results are shown in FIG. 6. No discernible signal was obtained in the presence of agonist alone (no modulator). In the presence of agonist together with modulator, a significant increase in agonist activity was seen.

What is claimed is:

1. A method for identifying an efficacy enhancer of an angonist of an α7-nicotinic receptor, said method comprising the steps of: (a) expressing said nicotinic receptor on the surface of a cell; (b) contacting said nicotinic receptor with a compound known to be a nicotinic receptor agonist and a compound to be tested for efficacy enhancement activity; and, (c) determining whether said compound to be tested exhibits enhancement of an effect of said nicotinic receptor agonist.

2. A method for identifying a compound which is an agonist of an α7-nicotinic receptor, said method comprising the steps of: (a) expressing said nicotinic receptor on the surface of a cell; (b) contacting said nicotinic receptor with a compound to be tested nicotinic receptor agonist activity, in the presence of an efficacy enhancer of a nicotinic receptor agonist; and, (c) determining whether said compound to be tested exhibits nicotinic receptor agonist activity.

* * * * *